US005679806A

United States Patent [19]
Zheng et al.

[11] Patent Number: 5,679,806
[45] Date of Patent: Oct. 21, 1997

[54] PROCESS FOR THE ISOLATION AND PURIFICATION OF ISOFLAVONES

[75] Inventors: BoLin Zheng, Superior; John A. Yegge, Longmont; David T. Bailey, Boulder; James L. Sullivan, Louisville, all of Colo.

[73] Assignee: Hauser, Inc., Boulder, Colo.

[21] Appl. No.: 394,407

[22] Filed: Feb. 24, 1995

[51] Int. Cl.$^6$ .................. C07D 311/36; C07D 311/40
[52] U.S. Cl. ............................................. 549/403
[58] Field of Search ................................ 549/403

[56] References Cited

PUBLICATIONS

"Mechanism of Antioxidant Action of Pueraria Glycoside (PG)–1 (an Isoflavonoid) and Mangiferin (a Xanthonoid)," Takashi Sato et al., Chem. Pharm. Bull., 40(3):721–724, month not available (1992).

"Isolation and High Performance Liquid Chromatography (HPLC) of Isoflavonoids from the Pueraria Root," Yukio Ohshima et al., Planta medica pp. 250–254 month not available (1988).

"Induced Isoflavonoids from Copper Chloride–Treated Stems of Pueraria lobata,"Takashi Hakamatsuka et al., Phytochemistry, 30(5):1481–1482 month not available (1991).

"Isolation of New Isoflavone from Chinese Pueraria Flowers," Michinori Kubo et al., Chem. Pharm. Bull., 23(10:2449–2450, month not available (1975).

"Studies on the Constituents of Pueraria lobata V. A Trypotphan Derivative from Pueraria Flos," Jun–ei Kinjo et al., Chem. Pharm. Bull., 36(10):4171–4173, month not available (1988).

"Isoflavone Synthase from Cell Suspension Cultures of Pueraria lobata," Takashi Hakamatsuka et al., Chem. Pharm. Bull., 38(7):1942–1945, month not available (1990).

"Kudzu in the South: An old Alternative Crop," Hortscience, 26:498, month not available (1991).

"Herbal Tonic Cuts Hamsters' Alcohol Use," Science News, 144:319, (Nov. 13, 1993).

"Hamsters Take The Pledge After Ancient Chinese Cure," New Scientist, pp. 4–5, (Nov. 6, 1993).

"Isoflavone Gluosides Exist as Their 6"–0–Malonyl Esters in Pueraria lobata and its Cell Suspension Cultures," Hyung–Hwan Park et al., Chem. Pharm. Bull., 40(7) month not available (1978, 1980, 1992).

"A New Irisolidone–7–0–Glucoside and Tectoridin From Pueraria Species," Michinori Kubo and Keizo Fujita, Phytochemical Reports, 12:2547–2548, (1973).

"Isoflavonoids and the Other Constituents in Callus Tissues of Pueraria lobata," Koichi Takeya and Hideji Itokawa, Chem. Pharm. Bull., 30:1496–1499, month not available (1982).

"High–Performance Liquid Chromatographic System For A Wide Range of Naturally Occurring Glycosides," Hitomi Kaizuka and Kunio Takahashi, Journal of Chromatography, 258:135–146, month not available (1983).

"Studies on the Constituents of Pueraria lobata, III. Isoflavonoids and Related Compounds in the Roots and the Voluble Stems," Jun–ei Kinjo et al., Chem. Pharm. Bull., 35(12):4846–4850, month not available (1987).

"Genistin and its Aglucone, Genistein," E.D. Walter, J. Amer. Chem. Soc. 63:3273–3276, month not available (1941).

"Soybean Chemistry & Technology," Goss et al., 31 month not available (1944).

"Studies on the Constituents of Japanese and Chinese Crude Drugs. IV. On the Constituents of Pueraria Root. (2).," Yakugaku Zasshi, 8:688–691, month not available (1960).

"Studies on the Constituents of Pueraria lobata. IV. $^{1)}$—Chemical Constituents in the Flowers and the Leaves," Kinjo et al., Chem. Pharm Bull., 36(3):1174–1179, month not available (1988).

"Oleanene Sapogenols From Puerariae Radix," Jun–ei Kinjo et al., Chem. Pharm. Bull., 33(3):1293–1297, month not available (1985).

"Kudzu (Pueraria lobata) In New England," Bruce A. Sorrie and William D. Perkins, Rhodora, 90(863):340–343, (1988).

"Volatile Flavor Components of Puerariae Radix (Pueraria lobata Ohwi)," Mistuo Miyazawa and Hiromu Kameoka, Agric. Bio. Chem., 52(4):1053–1055, month not available (1988).

"Fruits and Vegetable Fight Some Cancers", Better Nutrition for Today's Living, 55(10):26, (Oct. 1993).

"Spicing up your Isoflavones and Phytosterols," University of California, Berkeley Wellness Letter, 10(1):1, (Oct. 1993).

"Can Tofu Stop Cancer?", Susan Brink, U.S. News & World Report, 114(21):77, (May 31, 1993).

"Genistein, a Dietary Derived Inhibitor of In Vitro Angiogenesis," Cancer Researcher Weekly, p. 23, (May 17, 1993).

"Red Clover: Herbal Healer," Rob McCaleb, Better Nutrition for Today's Living, 53(12):28, (Dec. 1991).

"Increasing Use of Soyfoods and their Potential Role in Cancer Prevention," Mark Messina and Virginia Messida, Journal of the American Dietetic Association, 91(7):836, (Jul. 1991).

(List continued on next page.)

Primary Examiner—Johann Richter
Assistant Examiner—Laura L. Stockton
Attorney, Agent, or Firm—Chrisman, Bynum & Johnson, P.C.; Steven C. Petersen

[57] ABSTRACT

The present invention relates to a process for the isolation and purification of isoflavones from a number of different biomass sources. More particularly, the present invention relates to a three-step process whereby a biomass containing isoflavones with a solvent thereby forming an extract that is subsequently fractionated using a reverse phase matrix in combination with a step gradient elution, wherein the resulting fractions eluted from the column contain specific isoflavones that are later crystallized. The purified isoflavone glycosides may then be hydrolyzed to their respective aglycone.

35 Claims, 6 Drawing Sheets

OTHER PUBLICATIONS

"Is This the Dawning of the Age of Soy?", Chilton's, Food Engineering, 65(10):32, (Oct. 1993).

"Meals that Heal. Fruit Salad that Builds Bones. Soup that Lowers Blood Pressure. The Nutraceutical Revolution is Here!", Carl Sherman, Health, 23(2):69, (Mar. 1991).

"Blocking Breast Cancer: Do Faulty Estrogen Receptors Make a Meaner, Tougher Tumor?", Kathy A. Fackelmann, Science News, 137(19):296, (1990).

"Separation of Soybean Isoflavones from Their 5–Hydroxy Derivatives by Thin–Layer Chromatography," L.C. Wang, Short Communications, pp. 296–298 month not available (1971).

"Isoflavonoid Constituents of Soybeans and Isolation of a New Acetyl Daidzin," Ohta et al., Agri Biol. Chem., 43(7):1415–1419,(1979).

"Removal of Phenolic Compounds from Soy Protein Extracts Using Activated Carbon," J.S.L. How and C.V. Morr, Journal of Food Science, 47:933–940, month not available (1982).

"Determination of Isoflavones in Soybean Flours, Protein Concentrates, and Isolates," Arthur C. Eldridge, J. Agric. Food Chem., 30(2):353–355, month not available (1982).

"Isolation of 6"–0–Acetylgenistin and 6"–0–Acetyldaidzin from Toasted Defatted Soyflakes," Efi Farmakalidis and Patricia A. Murphy, J. Agric. Food Chem., 33(3):385–389, month not available (1985).

"High–Performance Liquid Chromatographic Analysis of Phytoestrogens in Soy Protein Preparations with Ultraviolet, Electrochemical and Thermospray Mass Spectrometric Detection," K.D.R. Setchell and Mary Beth Welsh, Journal of Chromatography, 386:315–323, month not available (1987).

"Identification and Accumulation of Isoflavonoids and Isoflavone Glucosides in Soybean Leaves and Hypocotyls in Resistance Responses to Phytophthora megasperma f.sp. glycinea," Morris et at., Physiological and Molecular Plant Pathology 39:229–244, month not available (1991).

"Flavonoids of Various Prunus Species VI. The Flavonoids in the Wood of Prunus aequinoctialis, P. nipponica, P. maximow and P. avium," Masao Hasegawa, J. Am. Chem. Soc., 79:1738–1740, month not available (1957).

"Chemical Determination of Isoflavones," Edmund Cheng and Lester Yoder, Iowa Academy of Science, 65:220–223, month not available (1958).

"The Constituents of Pueraria Root," Chem. Pharm. Bull., 7:134–136, month not available (1959).

"Chemosystematics of the Leguminosae. Flavonoid and Isoflavonoid Patterns in the Tribe Genisteae," J.B. Harborne, Phytocemistry, 8:1449–1456, month not available (1969).

"Distribution of Flavonoids in the Genus Baptisia (Leguminosae)," Markham et al., Phytochemistry, 9:2359–2364, month not available (1970).

"14.2 Isoflavones," Harborne et al., The Flavonoids, pp. 746–757, month not available (1975).

"A New Isoflavone from Soya Beans," Naim et al., Phytochemistry, 12:169–170, month not available (1973).

"Chemical Studies on the Oriental Plant Drugs. XXXV. The Chemical Constituents of the Heartwood of Maackia amurensis var. buergeri," Takai et al., Chem. Pharm. Bull., 20(11):2488–2490, month not available (1972).

"Soybean Isoflavones. Characterization, Determination, and Antifungal Activity," Naim et al., J. Agric. Food Chemistry, 22:806–809, month not available (1979).

"β–Galactosidase–Inhibiting New Isoflavonoids Produced by Actinomycetes," Hazato et at., The Journal of Antibiotics, XXXII(3):217–222, month not available (1979).

"Organoleptic and Nutritional Effects of Phenolic Compounds on Oilseed Protein Products: A Review," F. Sosulski, Journal of the American Oil Chemists' Society, 56:711–715, month not available (1979).

"Isolation of a New Isoflavone Acetyl Glucoside, 6"–0–Acetyl Genistin, from Soybeans," Ohta et al., Agri. Biol. Chem., 44(2):469–470, month not available(1980).

"Soybean Isoflavones: Effect of Environment and Variety on Composition," Arthur C. Eldridge and William F. Kwolek, J. Agric. Food Chem., 31:394–396, month not available (1983).

"Stress Metabolite Accumulation, Bacterial Growth and Bacterial Immobilization During Host and Nonhost Responses of Soybean to Bacteria," William F. Fett and Susan B. Jones, Physiological Plant Pathology, 25:277–296, month not available (1984).

"Distribution of Odontoglossum Ringspot Virus in Apical Meristems of Infected Cymbidium Cultivars," A. Toussaint et al., Physiological Plant Pathology, 25:297–298, month not available (1984).

"Accumulation of Isoflavonoids and Isoflavone Gulcosides After Inoculation of Soybean Leaves with Xanthomonas campestris pv. glycines and pv. campestris and a Study of Their Role in Resistance," W.F. Fett, Physiological Plant Pathology, 24:303–320, month not available (1984).

"A Specific Inhibitor For Tyrosine Protein Kinase From Pseudomonas," Ogawars et al., The Journal of Antibiotics, XXXIX(4):606–608, (Apr. 1986).

"Investigation of the Isoflavone Content of a Commercial Variety of Lupinus luteus Using Thermospray Liquid–Chromatography Mass Spectrometry (TSP–LC–MS)," Pantry et al., Plant Flavonoids in Biology and Medicine II: Biochemical, Cellular, and Medicinal, month not available 1988 pp. 52–60.

"3. Isoflavones," CRC Critical Reviews in Food Science and Nutrition, 27(4):230–236, month not available (1988).

"Isotope Dilution Gas Chromatographic–Mass Spectrometric Method for the Determination of Lignans and Isoflavonoids in Human Urine, Including Identification of Genistein," Adlercreutz et al., Clinica Chimica Acta, 199:263–278, month not available (1991).

"Accumulation of Isoflavones in Lupin Seedings Treated with Copper Chloride," Shibuya et al., Biosci. Biotech. Biochem., 56(4):690–691, month not available (1992).

"The Antioxidants of Higher Plants," Richard A. Larson, Phytochemistry, 27(4):969–979, month not available (1988).

"Antioxidant and Pro–oxidant Actions of the Plant Phenolics Quercetin, Gossypol and Myricetin," Laughton et al., Chemical Pharmocology, 38(17):2859–2965, month not available (1989).

"Two Isoflavones from Flemingia philippinensis," Chen et.al., Phytochemistry, 30(11):3842–3845, month not available (1991).

"Isoflavones From Stems of Euchresta horsfieldII," Mizuno et al., Phytochemistry, 29(8), 2675–2677, month not available (1990).

"Malonyl Isoflavone Glycosides in Soybean Seeds," Kudou et al., Agri Biol. Chem., 55(9):2227–2233, month not available (1991).

"Genistein Inhibition of the Growth of Human Breast Cancer Cells: Independence From Estrogen Receptors and the Multi–Drug Resistance Gene," Peterson et al., *Biochemical and Biophysical Research Communications*, 179(1):661–667, (Aug. 30, 1991).

"High–Performance Liquid Chromatography Separation of Soybean Isoflavones and Their Glucosides," A.C. Eldridge, *Journal of Chromatography*, 234:494–496, month not available (1982).

"A New Isoflavone Glycoside in Soybean Seeds (*Glycine max* Merrill), Glycitein 7–0–β–D–(6"–0–Acetyl)–Glucopyranoside," Kudou et al., *Agric. Biol. Chem.*, 55(3):859–860, month not available (1991).

|    |                      | $R_1$          | $R_2$ | $R_3$ | $R_4$   |
|----|----------------------|----------------|-------|-------|---------|
| 1a | daidzin              | glucose        | H     | H     | H       |
| 1b | genistin             | glucose        | H     | OH    | H       |
| 1c | glycitein            | H              | OMe   | H     | H       |
| 1d | 6"-O-acetyl daidzin  | Acetyl glucose | H     | H     | H       |
| 1e | 6"-O-acetyl genistin | Acetyl glucose | H     | H     | H       |
| 1f | puerarin             | H              | H     | H     | glucose |
| 1g | 6"-O-malonyl daidzin | Malonyl glucose| H     | H     | H       |
| 1h | 6"-O-malonyl genistin| Malonyl glucose| H     | OH    | H       |

(the 6" position is on the glucose ring)

PROCESS FOR THE ISOLATION AND PURIFICATION OF ISOFLAVONES

BACKGROUND OF THE INVENTION

1. Field of the Invention

The present invention relates to a process for the isolation and purification of isoflavones from a number of different biomass sources. More particularly, the present invention relates to a three-step process whereby specific isoflavones are isolated and purified from plant materials such as *Glycine max* (soy) and *Pueraria lobata* (kudzu).

2. Description of the State of Art

The isoflavones are a group of naturally occurring plant compounds having the aromatic heterocyclic skeleton of flavan and which often possess estrogenic activity. Their existence in Glycine, Pueraria and other plant species has long been known. The roots of Pueraria are used under the name of Gegen in Chinese traditional medicine as the main component of a prescription, Gegen Tao, for the common cold. The Pueraria root contains several isoflavone compounds, such as daidzin (1a), puerarin (1f), and daidzein (2a), shown in FIGS. 1 and 2, respectively. Soy is known to contain the isoflavones, daidzin (1a), genistin (1b), glycitein (1c), 6"dadidzin-O-acetyl (1d), 6"-O-acetyl genistin (e), 6"-O-malonyl daidzin (1g), 6"-O-malonyl genistin (1h), also shown in FIG. 1. It has been reported that these isoflavone compounds possess antihemolytic, antioxidative, antifungal, estrogenic and antitumor activities, and also are the source of the undesirable bitter and astringent tastes characteristic in soybean. Recent studies suggest that the isoflavones daidzin and daidzein work to suppress the desire for alcohol; while genistin and genistein may block the formation of new blood vessels which are needed to nourish malignant tumors.

A variety of different procedures for isolating and purifying isoflavones from plant materials have been published. The reference that is most prevalently cited throughout the literature is Ohshima et al., Planta Medica, 250–254 (1988). Ohshima at al., discloses a method of extracting Pueraria root, using acetone to first extract the non-glycosidic flavonoids. The dried root is then extracted with methanol, the methanolic extract is subsequently re-extracted with aqueous butanol, and the resulting butanol layer is passed over a chromatographic column, eluting with methanol. The resulting glycosidic fractions are further chromatographed over a silica gel column followed by two preparative high performance liquid chromatography columns. Ohta et al., Agric Biol. Chem., 43:7, 1415–1419 (1979) discloses a method of isolating and purifying isoflavones from defatted soybeans whereby the defatted soybeans are extracted with ethanol and the resulting ethanol extracts are treated with acetone and ethyl acetate. The ethyl acetate extract is then fractionated over silica gel and Sephadex LH-20 columns followed by multiple recrystallizations. Farmakalidis et al., reported in the Journal of Agric. Food Chem., 33:385–389 (1985) that acetone when mixed with 0.1N HCl was superior over 80% methanol as an extraction solvent. The subsequent isolation procedure followed by Farmakalidis et al. was that of Ohta et al., discussed previously. E. D. Walter published a method for the extraction and isolation of genistin and its aglycone, genistein, from soybeans, J. Amer. Chem. Soc., 63:3273–3276 (1941). 10 Kg of defatted soybean flakes having been extracted with hexane are twice extracted using methanol. Acetone is added to the combined methanolic extract to precipitate some of the phosphatides and other impurities. The supernatant is decanted and two volumes of water are added to precipitate out the genistin. Multiple recrystallizations are then performed to purify the genistin. The above technical papers by Ohshima et al., Ohta et al., and Farmakalidis et al. are just a few examples of the many processes that currently exist in the literature, whereby isoflavones are extracted, isolated and purified from various plant materials. However each process disclosed involves multiple steps and various solvents. Consequently, the disclosed laboratory scale processes are not easily scaled up to an efficient commercial process where disposal considerations of various solvents play an important role in the overall feasibility of the process. A further disadvantage of the processes as disclosed in the literature is the requirement of multiple chromatography columns. The eluants utilized by various researchers in the field typically separate the isoflavones from other compounds present in the plant extract. However, upon isolation of the isoflavone compounds further separation techniques involving chromatography are required. These separation techniques necessitate the continuous need to monitor the eluant as it runs off the column, thus making it possible to collect those fractions of eluant that contain a particular isoflavone. The Walter article which eliminated the necessity of chromatography only isolated one isoflavone, genistin.

There is still a need, therefore, for a process and procedure for isolating and purifying isoflavones from isoflavone containing biomass in a commercially viable manner which directly provides a high concentration of the various isoflavones which can be subsequently recovered in high yield and purity.

SUMMARY OF THE INVENTION

Accordingly, it is an object of this invention to provide a simplified method for the extraction, isolation and purification of specific isoflavones.

Another object of the present invention is to convert resulting isoflavone glycosides to their respective aglycones.

Additional objects, advantages, and novel features of this invention shall be set forth in part in the description and examples that follow, and in part will become apparent to those skilled in the art upon examination of the following specification or may be learned by the practice of the invention. The objects and advantages of the invention may be realized and attained by means of instrumentalities, combinations, compositions, and methods particularly pointed out in the appended claims.

To achieve the foregoing and other objects and in accordance with the purposes of the present invention, as embodied and broadly described therein the method of this invention comprises contacting any plant material containing isoflavones with a solvent thereby forming an extract that is subsequently fractionated using a reverse phase matrix, wherein the resulting fractions eluted from the column contain specific isoflavones that are later crystallized. The purified isoflavone glycosides may then be hydrolyzed if so desired to their respective aglycones.

BRIEF DESCRIPTION OF THE DRAWINGS

The accompanying drawings, which are incorporated in and form a part of the specifications, illustrate the preferred embodiments of the present invention, and together with the description serve to explain the principles of the invention.

In the Drawing.

DETAILED DESCRIPTION OF THE PREFERRED EMBODIMENT

Figure 1:
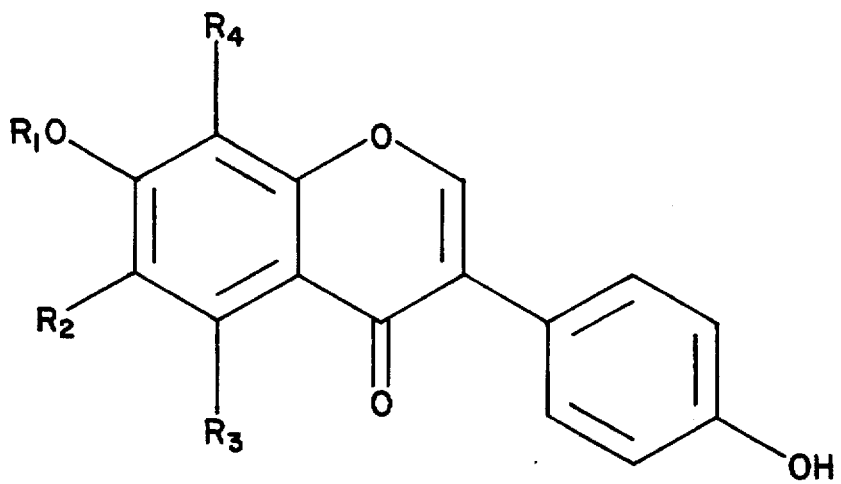
FIG. 1 shows the structure of specific isoflavones.
Figure 2:
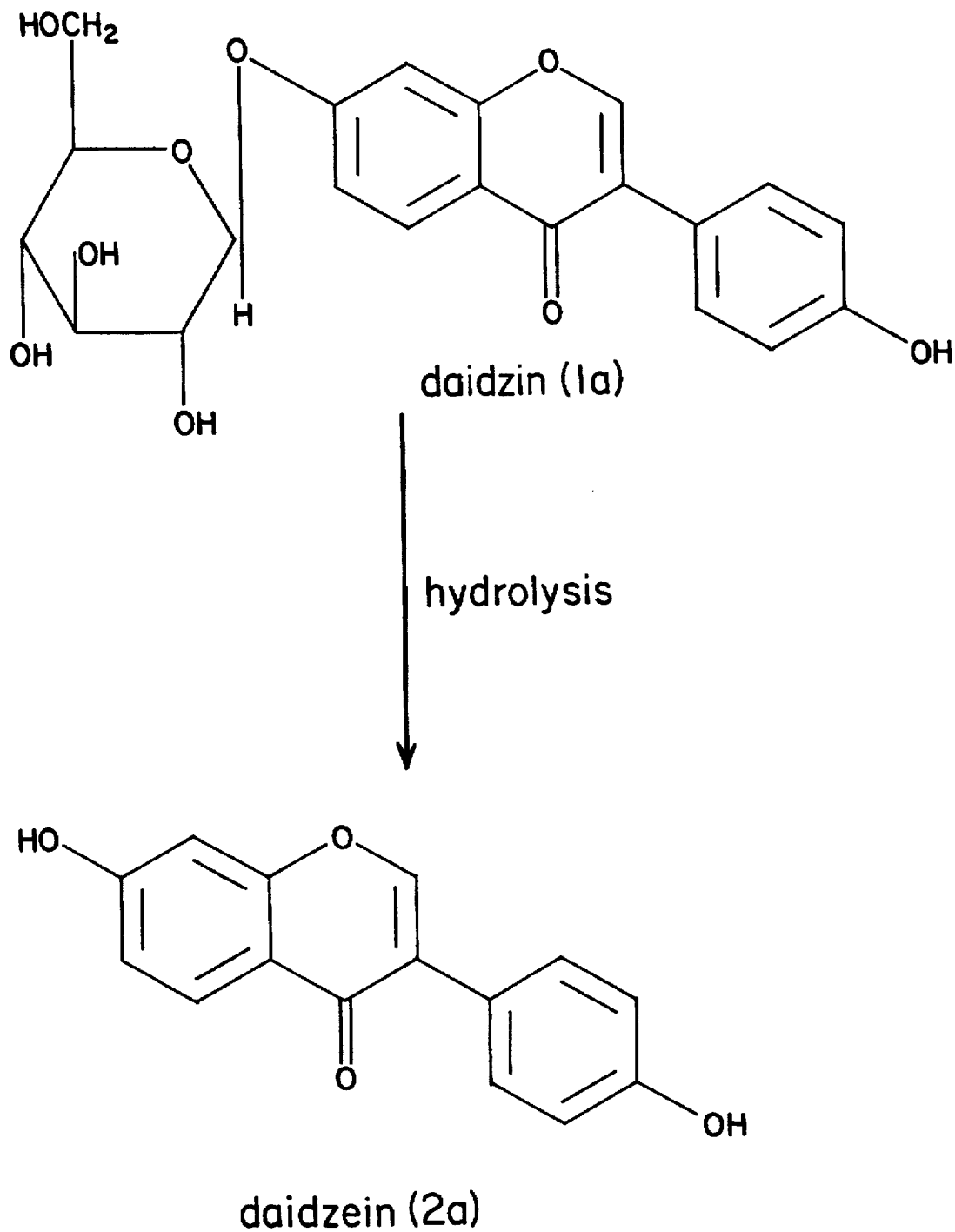
FIG. 2 shows the resulting structure, daidzein, upon hydrolysis of daidzin.
Figure 3:
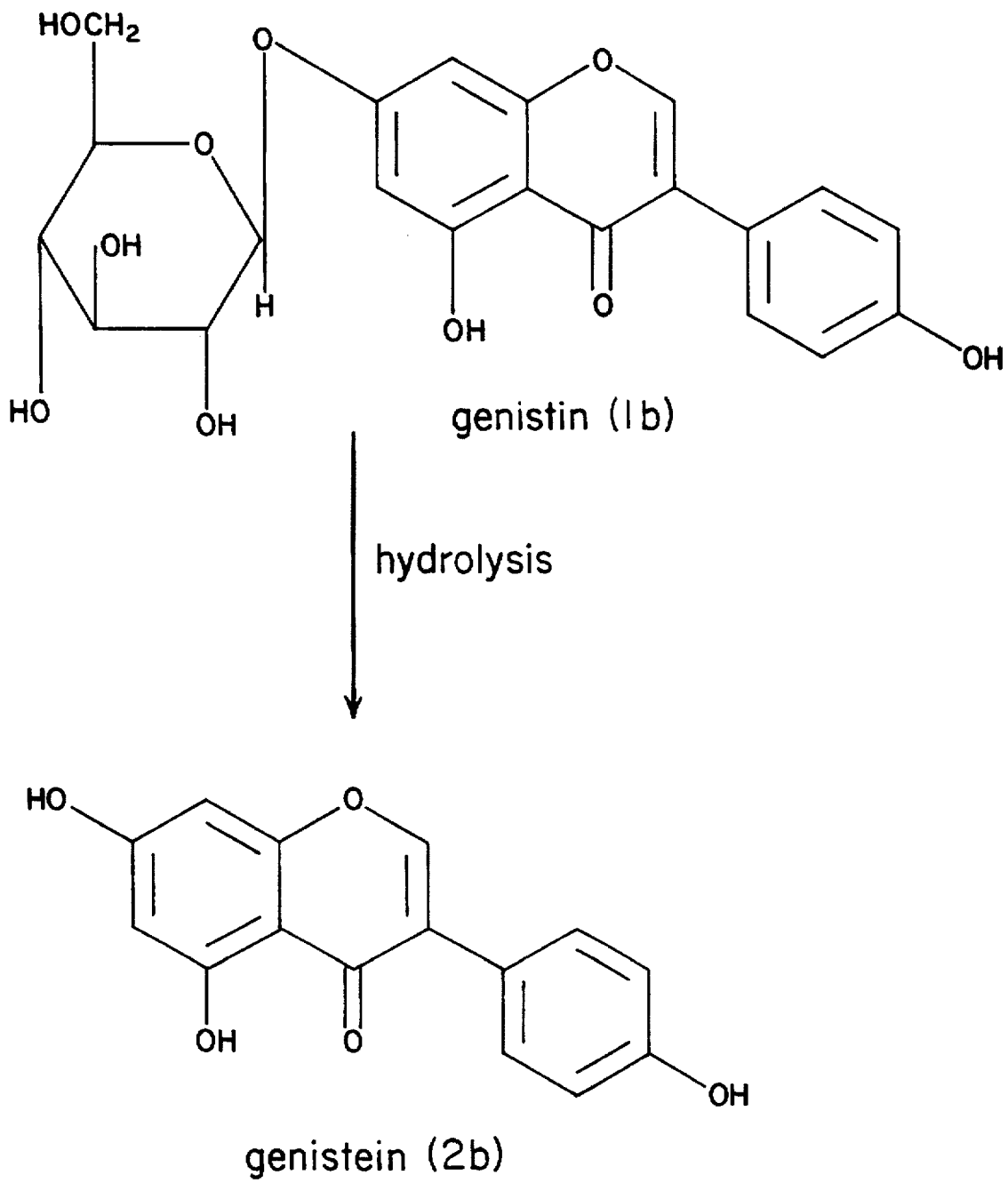
FIG. 3 shows the resulting structure, genistein, upon hydrolysis of genistin.

In general the present invention relates to a high yield process for the isolation and purification of the isoflavones appropriate to a particular plant material which includes but is not limited to partially purified plant derivatives, shown in FIGS. 1, 2 and 3. The purified isoflavone glycosides may then be easily converted by acid hydrolysis to their respective aglycone. The preferred embodiment of the present invention is a three step process and is described in detail below. The first step includes contacting a plant material that contains isoflavones with a solvent, thus resulting in a crude extract containing a mixture of compounds that includes isoflavones. The second step involves adsorbing the isoflavone compounds onto a reverse phase matrix followed by the specific desorption of certain isoflavones from the matrix in fractions using a step gradient elution, and then evaporating selected pools. The third and final step involves crystallization to achieve a final high purity product. The thus purified isoflavone glycosides may then, if desired, be contacted with an acid to effectively cleave the glucose molecule, resulting in an aglycone that can be subsequently crystallized.

This invention includes a process for the extraction, isolation and purification of isoflavones from plant materials or biomasses that contain isoflavones. As way of illustration only, the following is a partial list of plant sources containing isoflavones: *Pueraria lobata, Glycine max*, Thermospin sp., Baptisia sp., Trifolium sp., etc. Again, this list is exemplary of the plant materials that contain isoflavones, and is not meant to limit the scope of plant materials which may be utilized by the present invention. The first step in the process of the present invention, extraction of the isoflavone compounds, is preferably accomplished by mixing or contacting a first solvent, such as an alcohol, and preferably ethanol or methanol with a plant material containing isoflavones. Depending on the type of plant material used, it may be necessary to grind it into a range of 0.1–10 min. The degree of comminutation of the plant material should provide sufficient particulate surface area for the first solvent to contact, but again this depends on the type of plant material used. The skilled person in this art will recognize that a variety of extraction methods are available in the literature, such as, percolation, vat extraction, counter-current extraction, etc. The particular method of extraction employed is not essential to the process of the present invention. In the extraction process, the temperature of extraction is between 40°–70° C., with 50°–60° C. being preferred. The mount of plant material to solvent mixture used in the extraction process varies between 1:1 to 1:10 on a gram:milliliter basis, with 1:1 to 1:3 being preferred. The isoflavones and some of the extraneous materials that are contained in the comminuted plant material are soluble in the first solvent used. Thus, the first solvent, the isoflavones and some of the extraneous materials form the crude extract.

The crude alcohol extract is next diluted with distilled water to a final volume of 20% alcohol in water. The resulting solution is then filtered to remove insoluble materials.

Figure 4:
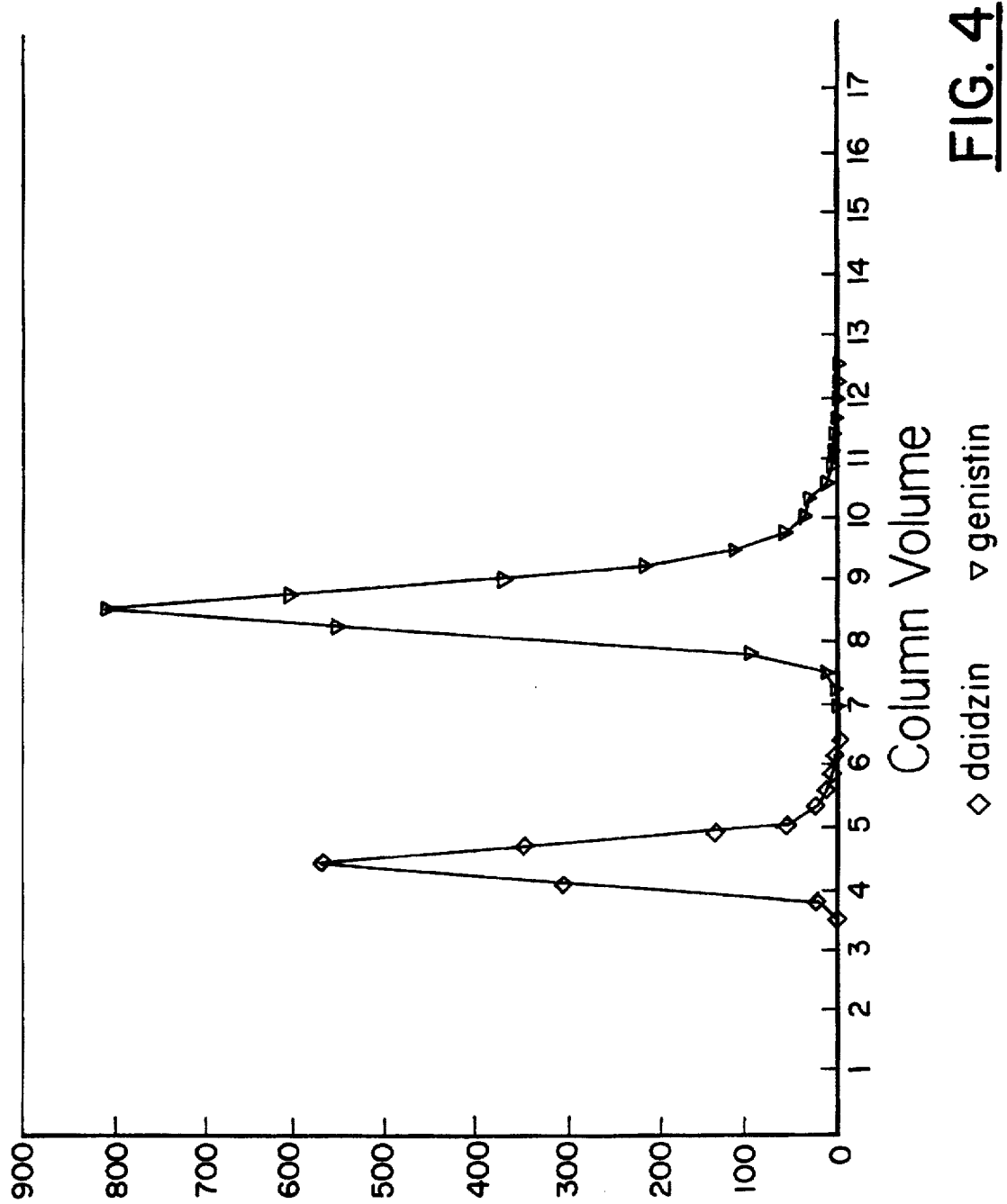
FIG. 4 shows a chromatographic separation of daidzin and genistin from defatted soy flakes.

After completion of the formation of the crude extract, the second step, the separation of the isoflavones, begins. Since the crude extract contains not only the desired isoflavones but also extraneous materials that are soluble in the first solvent of the crude extract, it is desirable to recover the isoflavones with as little extraneous material as possible. The following step, of the isolation of the isoflavones from the crude extract, includes the partial elimination of unwanted extraneous materials such as phenols, $H_2O$, proteins, simple and complex sugars, etc., while selectively maintaining the isoflavones. To recover the isoflavones the water diluted crude extract is loaded onto a reverse phase matrix. In this step the preferred adsorbent is polymethacrylate or C-18. Subsequent to adsorbing the isoflavones to the matrix, groups of isoflavones are specifically desorbed from the matrix and eluted in fractions using a series of specific solvents each having a volume five times that of the column that supports the matrix and comprising a specific ratio of a second solvent, such as an alcohol to water. The preferred alcohol is methanol or ethanol. Molecules having the lowest affinity for the adsorbent are specifically desorbed passing directly through the matrix and collected in the first wash column volume. With each successive column volume of eluting solvent the specific ratio of the second solvent to water increases and the isoflavones are specifically desorbed in sequence according to their affinity for the adsorbent. FIG. 4 illustrates a typical chromatogram for soy having retention values in column volumes for the various isoflavones. The horizontal axis represents the total volume of eluting solvent put through the column. Each step in the gradient has a volume five times that of the column; therefore, 0–5.0 column volumes represents the first step in the gradient, while 5.1–10 column volumes represents the second step in the gradient and so on. As shown in FIG. 4, the first major peak begins at approximately column volume 3.8 and ends around column volume 5.0. The isoflavone represented by that peak is said to elute in a total of 1.2 column volumes. Since these numbers fall between 0 and 5.0 it can also be determined which step in the gradient and thus the ratio of the second solvent to water necessary to desorb that specific isoflavone. It is important that the ratio of the second solvent to water increases with each step as opposed to decreasing. If a large alcohol ratio was used in the first step, those isoflavones having a higher relative affinity toward the adsorbent would desorb along with those isoflavones having a lower relative affinity for the adsorbent and thus no separation would be achieved. Each pool collected represents a distinct major isoflavone. The individual pools are evaporated resulting in a solid or crude product of each desired isoflavone.

The preferred third and final step in the process is the crystallization or final purification of each isoflavone. To begin, the dried crude product of one isoflavone from the preceding step is dissolved (1 mg/ml) in a volume of solvent, the preferred solvent is methanol, however ethanol will also suffice. The resulting suspension is decolorized by the addition of active carbon that is subsequently removed by passing the suspension through a filter aid, such as celite. The volume of the decolorized solution is evaporated to a final ratio of 10–60 mg of isoflavone per ml of solvent and is then crystallized by refrigerating the solution overnight. The refrigerated suspension is then passed through a filter and the final product, the crystallized isoflavone, is collected and dried.

There is some evidence in the research literature that the isoflavone aglycones may have more biological activity than their respective glycosides. However, isoflavone aglycones are found in very low abundance in plant tissues. Therefore, the present invention also contemplates the hydrolysis of the isoflavone glycosides to form their respective aglycones. Cleavage of the glucose, acetylglucose or malonylglucose molecule from an isoflavone glycoside may be accomplished by subjecting the isoflavone glycoside to acid hydrolysis in HCl-water, preferably 4N HCl at 100° C. for 5 hours. The benefits of an acid/water hydrolysis are the elimination of organic solvents and ease of recovery of the product by filtration. Following the hydrolysis, the isoflavone aglycone is recovered by filtration, dried, and may then be crystallized from methanol, as discussed above, or alternatively extracted with diethyl ether, evaporated, and recrystallized from alcohol as discussed in further detail in the Examples which follow.

The following non-limited examples provide specific high yield processes for isolating and purifying isoflavones from plant tissues. All scientific and technical terms have the meanings as understood by one with ordinary skill in the art. Melting points were measured on a MEL-TEMP II apparatus equipped with a Barnant 100 Thermocouple Thermometer and are uncorrected. HPLC was performed on a Hitachi chromatograph (L-6200 Intelligent Pump, D-6000 Interface, L-4000 UV Detector and AS-4000 Intelligent Auto Sampler). Combinations of acetonitrile and water (2% acetic acid) in different concentrations were used as the HPLC solvent system. Commercially available chemicals were used without any further purification. NMR was performed on a JEOL Eclipse 400. Centrifugation was done on a Beckman Model CS 6KR centrifuge.

EXAMPLE I

Figure 5:
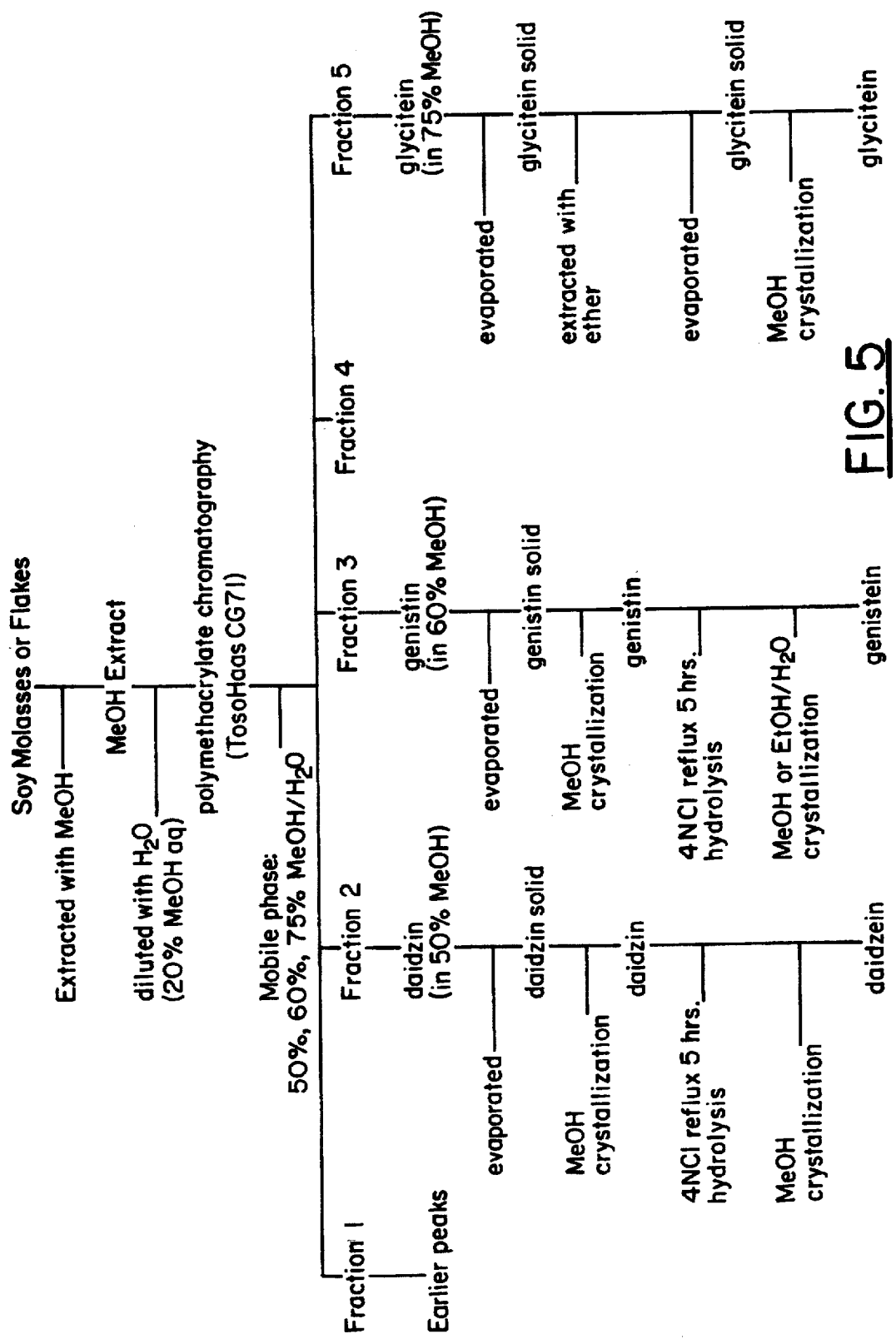
FIG. 5 shows a flow diagram for the extraction and isolation procedure for isoflavones from soy products.

The entire isolation and purification procedure for isoflavones from soy molasses discussed in detail below is represented in the flow diagram depicted in FIG. 5.

A. Methanol extraction of soy molasses:

Approximately 1544 grams of soy molasses were introduced into a beaker having 900 ml of methanol and a magnetic stir bar. The mixture was then stirred at 50°–60° C. for 30 minutes and the solids were removed by centrifugation for 30 minutes. These solids were reextracted with 900 ml of methanol at 50°–60° C. for 30 minutes, centrifuged, and the two supernatants combined to form a crude extract. HPLC analysis of the extracts showed daidzin at 5.83 mg/ml with a purity of 1.3% and genistin at 6.46 mg/ml with a purity of 1.5%.

B. Specific adsorption/desorption separation using a reverse phase matrix:

About 1.8 L of the methanol extract of soy molasses was diluted with distilled water to make a 20% methanol in water solution which was loaded onto a properly conditioned 4"×70" polymethacrylate column and gradually eluted step-wise with five column volumes each of 50%, 60%, and 75% methanol in water. The eluant was collected in 100 ml fractions as it came off the bottom of the column and analyzed for the presence of isoflavones by HPLC. The first step gradient of 50% methanol in water was represented by a pool eluted between 0–5 total column volumes. Daidzin eluted from the column in the fraction which was represented by a pool eluted between 2.8–4.1 total column volumes. Genistin was eluted with the second step gradient of 60% methanol in water in a pool eluted between 6.3–8.0 total column volumes. Glycitein was eluted from the column using the third step gradient of 75 % methanol in water in a pool eluted between 11.9–13.3 total column volumes. The individual product pools were taken to dryness resulting in dry crude products.

C. Crystallization:

About 5.87 grams of daidzin crude product (62% purity) were dissolved in 300 ml methanol, followed by the addition of active carbon to decolorize the solution. The active carbon was removed by filtration and the solution was evaporated to 120 ml and refrigerated overnight. The suspension was then filtered and the final product, 2.9 grams of daidzin crystals were recovered resulting in an 80% recovery having a 97% purity. Daidzin m.p. 225°–225.8° C. $^1$H NMR (400 MHz, DMSO-$d_6$) δ:6.83 (2H, d, J=8 Hz, H-3'), 7.13 (1H, dd, J=8, 2 Hz, H-6), 7.23 (1H, d, J=2 Hz, H-8), 7.42 (2H, d, J=8 Hz, H-2'), 8.06 (1H, d, J=8 Hz, H-5), 8.38 (1H, s, H-2), 9.55 (1H, s, 4'-OH). $^{13}$C NMR (100 MHz, DMSO-$d_6$) δ:153.8, 124.2, 175.2, 127.5, 115.5, 161.4, 103.9, 157.5, 119.0, 122.8, 130.6, 115.5, 157.8, 103.9, 73.6, 77.0, 70.1, 77.7, 60.9.

D. Hydrolysis and Crystallization:

987.3 mg of daidzin were refluxed in 470 ml 4N HCl for five hours at 105°±5° C. About 554.1 mg of daidzein was recovered by filtration which resulted in a 92% recovery. About 442.9 mg of this recovered daidzein from the hydrolysis step was dissolved in 200 ml methanol and crystallized in 30 ml methanol. About 339.0 mg daidzein crystal was obtained with 77% recovery and about 99% purity.

EXAMPLE II

The entire isolation and purification procedure from defatted soy flakes discussed in detail below is represented in the flow diagram depicted in FIG. 5.

A. Methanol extraction of defatted soy flakes:

Approximately 909 grams of defatted soy flakes were introduced into a beaker having 2 L of methanol and a magnetic stir bar. The mixture was then stirred at 55° C. for 30 minutes and the solids were removed by filtration. These solids were extracted four more times each with 2 L of methanol at 55° for 30 minutes, filtered and the five filtrates combined to form the crude extract. HPLC analysis of the extract showed about 485 mg daidzin and 636 mg genistin. Two earlier eluting peaks were identified as 6"-O-malonyl daidzin and 6"-O-malonyl genistin.

B. Specific adsorption/desorption separation using a reverse phase matrix:

About 9 L of defatted soy flakes methanol extract were diluted with distilled water to make a 20% methanol in water solution which was then loaded onto a properly conditioned 4"×70" polymethacrylate column and gradually eluted stepwise with five column volumes each of 50%, 60%, and 75% methanol in water. The eluant was collected in 100 ml fractions as it came off the bottom of the column and analyzed for the presence of isoflavones by HPLC. The first step gradient of 50% methanol in water represented column volumes from 0–5. 6"-O-malonyl daidzin, 6"-O-malonyl genistin and daidzin eluted from the column in the fractions which were represented by a pool eluted between 0–1.3, 1.0–1.6 and 3.5–6.1 column volumes respectively. Genistin was eluted with the second step gradient of 60% methanol in water in a pool between 7.0–10.0 total column volumes. The individual pools were taken to dryness resulting in 396 mg of daidzin and 515 mg of genistin.

C. Crystallization:

About 0.727 grams of genistin crude product (63% purity) were dissolved in 250 ml methanol, followed by the addition of active carbon to decolorize the solution. The active carbon was then removed by filtration and the solution was evaporated to 22 ml and refrigerated overnight. The suspension was then filtered and the final product, 0.339 grams crystalline genistin were recovered with a 97% purity and 72% recovery. Genistin m.p.250.8°–252.0° C. $^1$H NMR (400 MHz, DMSO-d$_6$) δ:6.47 (1H, d, J=2 Hz, H-6), 6.72 (1H, d, J=2 Hz, H-8), 12.92 (1H, s, H-5), 6.83 (2H, d, J=8 Hz, H-3'), 7.39 (2H, d, J=8 Hz, H-2$^1$), 8.39 (1H, s, H-2), 9.61 (1H, s, 4$^1$-OH), 12.92 (1H, s, 5-OH). $^{13}$C NMR (100 MHz, DMSO-d$_6$) 154.6, 123.1, 181.0, 162.1, 100.1, 163.5, 95.0, 157.7, 106.6, 121.5, 130.7, 115.6, 157.7, 100.4, 73.6, 76.9, 70.1, 77.7, 60.0.

D. Genistein via Hydrolysis and Crystallization:

About 49.0 mg of genistin were refluxed in 15 ml 4N HCl for five hours at 105°±5° C. About 22.9 mg of genistein was obtained with about 75% recovery. About 13 mg genistein from the previous step was extracted twice with 50 ml diethyl ether. The extracts were combined, and evaporated to dryness. The solids obtained were crystallized from 2 ml of a solution made from 3 parts ethanol and 2 parts water. About 8.2 mg of the genistein crystal was obtained with 63% recovery and about 99% purity.

EXAMPLE III

The genistin used in the present Example was obtained in the same manner as described in Example I above from soy molasses.

D. Hydrolysis and Crystallization:

About 1578 mg of genistin were refluxed in 960 ml 4N HCl for five hours at 100°±5° C. About 948 mg genistein were obtained with about 96% recovery. 483.2 mg of genistein (99% purity) recovered from the hydrolysis step was dissolved in 450 ml methanol and crystallized in 20 ml methanol. About 373.8 mg of genistein crystal was obtained giving a 77% recovery and 99.5% purity. Genistein m.p. 298.4°–299.9° C. $^1$H NMR (400 MHz, DMSO-d$_6$) 6.22 (1H, d, J=2 Hz, H-8), 6.38 (1H, d, J=2 Hz, H-6), 6.83 (2H, d, J=8 Hz, H-3'), 7.39 (2H, d, J=8 Hz, H-2'), 8.43 (1H, s, H-2), 9.61 (1H, s, 4'-OH), 10.90 (1H, s, 7-OH) 12.92 (1H, s, 5-OH). $^{13}$C NMR (100 MHz, DMSO-d$_6$) 154.5, 122.8, 180.7, 162.5, 99.5, 164.8, 94.2, 157.9, 105.0, 121.7, 130.7, 115.6, 158.1.

EXAMPLE IV

Figure 6:
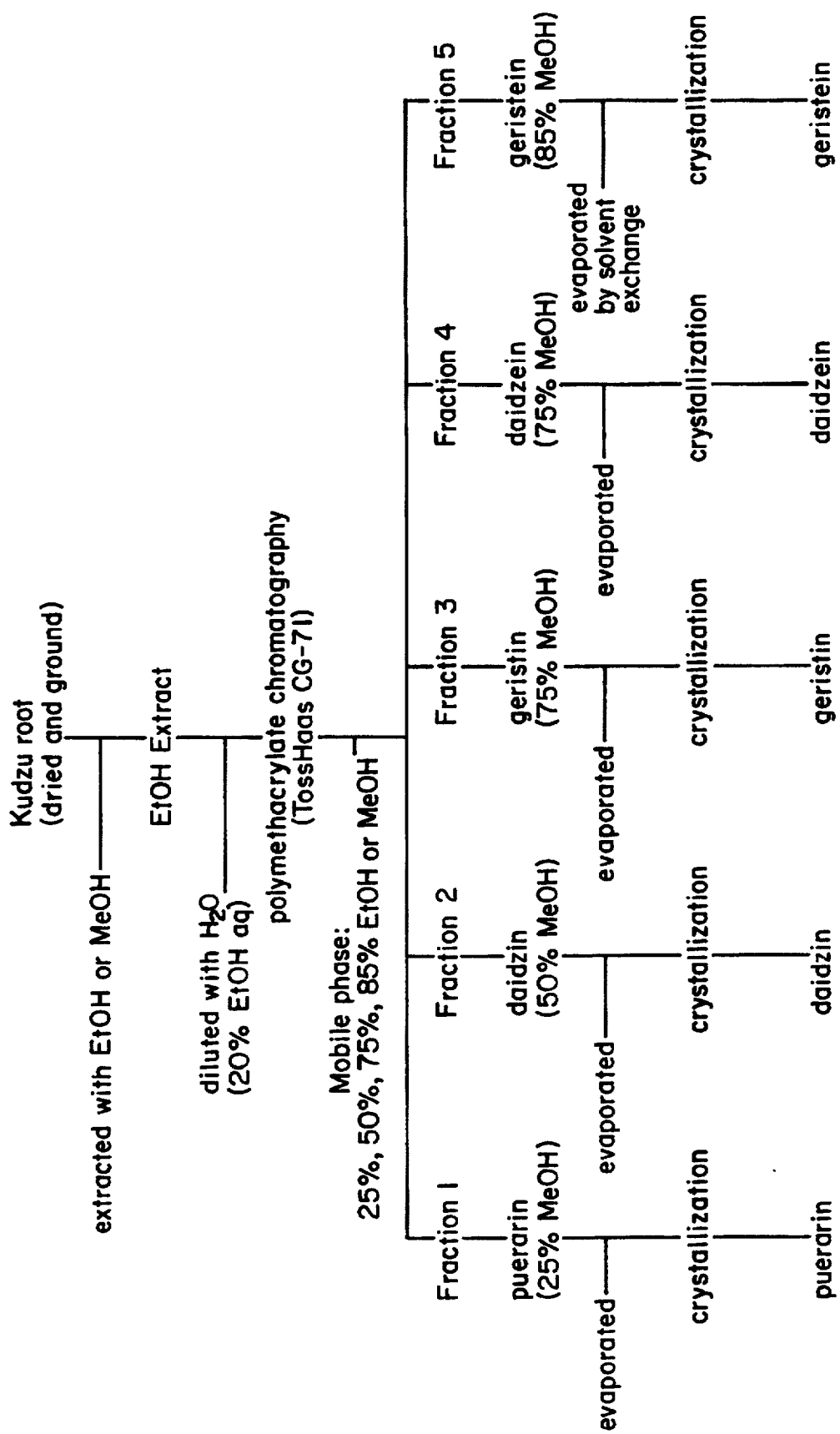
FIG. 6 shows a flow diagram for the extraction and isolation procedure for isoflavones from Pueraria.

The entire isolation and purification procedure from dry kudzu root discussed in detail below is represented in the flow diagram depicted in FIG. 6.

A. Ethanol extraction of dry kudzu Pueraria lobataroot:

Approximately 137 grams of dry kudzu root, 1.68% (w/w) isoflavones in dry biomass were introduced into a beaker having 600 ml of 95% ethanol and a magnetic stir bar. The mixture was then stirred at 55° C. for 30 minutes and the solids were removed by centrifugation for 30 minutes. These solids were extracted two more times with 600 ml of methanol at 55° C. for 30 minutes, centrifuged, and the three supernatants combined and evaporated to form a crude extract. HPLC analysis of the supernatants showed the total isoflavones in the extract to be 26% (w/w).

B. Specie adsorption/desorption separation using a reverse phase matrix:

About 50 ml of kudzu ethanol extract were diluted with distilled water to make a 20% ethanol in water solution which was then loaded onto a properly conditioned 1.5×20.3 cm polymethacrylate column and gradually eluted stepwise with five column volumes each of 25%, 50%, 75%, and 85% methanol in water. The eluant was collected in 20 ml fractions as it came off the bottom of the column and analyzed for the presence of isoflavones by HPLC. The first step gradient of 25% methanol in water was represented by a pool eluting between 0–5 column volumes. The second step gradient of 50% methanol in water was represented by a pool eluting between 5–10 column volumes, etc. Puerarin and daidzin eluted from the column in the fractions eluting between 6.7–9.0 and 9.2–10.9 total column volumes, respectively. Genistin was eluted with the third step gradient of 75% methanol in water eluting in a pool between 12.2–13.8 total column volumes. Daidzein and genistein were eluted from the column using the fourth step gradient of 85% methanol in water and was represented by a pool eluting between 15.2–16.8, and 17.7–19.3 column volumes, respectively. Ethanol in water was also used as a gradient elution solvent in this case. The individual pools were taken to dryness resulting in a dry solid or crude product.

C. Crystallization:

The procedure set out in Example I above was followed.

D. Hydrolysis and Crystallization:

The procedure set out in Example I above was followed. Daidzein m.p. 315.2–325.4 (dec.). $^1$H NMR (400 MHz, DMSO-d$_6$) 6.81 (2H, d, J=2 and 8 Hz, H-3'), 6.86 (1H, d, J=2 Hz, H-8), 6.94 (1H, dd, J-=8, 2 Hz, H-6), 7.43 (2H, d, J=8 Hz, H-2'), 7.97 (1H, d, J=8 Hz, H-5), 8.38 (1H, s, H-2), 9.5 (1H, s, 4'-OH), 10.7 (1H, s, 7-OH). $^{13}$C NMR (100 MHz, DMSO-d$_6$) 153.3, 124.0, 175.2, 127.8, 115.4, 163.0, 102.6, 157.9, 117.1, 123.0, 130.6, 115.6, 157.7.

The foregoing description is considered as illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

The embodiments of the invention in which an exclusive property or privilege is claimed are defined as follows:

1. A method of isolating isoflavones from any plant material that contains one or more type of isoflavone compounds, comprising the steps of:

contacting the plant material for a selected period of time with a first solvent whereby at least some of said isoflavone compounds are soluble and transported into said first solvent thereby forming a crude extract;

passing said crude extract through a column wherein said column contains an absorbent for specifically adsorbing said isoflavone compounds;

desorbing said isoflavone compounds sequentially from said adsorbent by flowing a series of eluant mixtures making up a step gradient elution over said column; and collecting each of the individual eluant mixtures of said step gradient elution flowing through said column wherein each of said individual eluant mixture contains primarily isoflavone compound.

2. The method of claim 1, wherein said individual eluant mixtures have specific ratios of a second solvent in the range of 25–85% to water.

3. The method of claim 1, wherein said first solvent is an alcohol.

4. The method of claim 2, wherein said second solvent is an alcohol.

5. The method of claim 4, wherein said alcohol is methanol.

6. The method of claim 4, wherein said alcohol is ethanol.

7. The method of claim 1, wherein said adsorbent is a reverse phase matrix.

8. The method of claim 7, wherein said reverse phase matrix is polymethacrylate.

9. The method of claim 7, wherein said reverse phase matrix is C-18.

10. The method of claim 1, wherein the plant material is soy.

11. The method of claim 1, wherein said plant material is soy molasses.

12. The method of claim 1, wherein said plant material is defatted soy flakes.

13. The method of claim 1, wherein said plant material is kudzu root.

14. The method of claim 1, further comprising the step of drying said individual eluant mixtures to obtain a crude product.

15. The method of claim 14, further comprising the step of crystallizing said crude product.

16. The method of claim 15, further comprising the step of hydrolyzing said crystalline product.

17. The method of claim 16 further comprising the step of crystallizing said hydrolyzed product.

18. A method of isolating isoflavones from any plant material that contains one or more isoflavone compounds, comprising the steps of:

contacting the plant material for a selected period of time with a first solvent whereby at least some of said isoflavone compounds are soluble or transported into said first solvent thereby forming a crude extract;

passing said crude extract having one or more of said isoflavone compounds through a low pressure column wherein said low pressure column contains an adsorbent for specifically adsorbing said isoflavone compounds;

desorbing said isoflavone compounds one at a time from said adsorbent by sequentially flowing a series of eluants over said adsorbent, wherein each eluant in said series comprises a specific ratio of a second solvent to water that specifically desorbs and transports at least one isoflavone compound; and collecting separately, each of said eluants transporting a specific isoflavone compound.

19. The method of claim 18, wherein each of said eluants are evaporated to a dry solid.

20. The method of claim 18, wherein said first solvent is an alcohol.

21. The method of claim 19, wherein said second solvent is an alcohol.

22. The method of claim 21, wherein said alcohol is methanol.

23. The method of claim 21, wherein said alcohol is ethanol.

24. The method of claim 18, wherein said adsorbent is a reverse phase matrix.

25. The method of claim 24, wherein said reverse phase matrix is polymethacrylate.

26. The method of claim 24, wherein said reverse phase matrix is C-18.

27. The method of claim 18, wherein the plant material is a soy.

28. The method of claim 18, wherein said plant material is soy molasses.

29. The method of claim 18, wherein said plant material is defatted soy flakes.

30. The method of claim 18, wherein said plant material is kudzu root.

31. The method of claim 19, further comprising the step of crystallizing said dry solid.

32. A method of isolating isoflavones from any plant material that contains one or more isoflavone compounds, comprising the steps of:

extracting one or more isoflavone compounds from the plant material;

adsorbing said isoflavone compounds to a reverse phase matrix;

desorbing a first isoflavone compound from said reverse phase matrix by flowing a first eluant having a ratio of a solvent to water over said matrix;

collecting said first eluant after said first eluant has flowed over said matrix;

desorbing a second isoflavone compound from said reverse phase matrix by flowing a second eluant, having a ratio of said solvent to water which is higher than the ratio of said solvent to water making up said first eluant, over said matrix; and collecting said second eluant after said second eluant has flowed over said matrix.

33. The method of claim 1, wherein said column is for low pressure chromatography.

34. The method of claim 31, further comprising the step of hydrolyzing said crystallized product.

35. The method of claim 1, further comprising the step of diluting said crude extract with water prior to passing said crude extract through said column.

* * * * *